United States Patent
Walkowiak et al.

(10) Patent No.: US 11,338,283 B2
(45) Date of Patent: May 24, 2022

(54) KIT FOR CENTRIFUGAL SEPARATION OF BIOLOGICAL FLUID COMPONENTS AND A METHOD FOR CENTRIFUGAL SEPARATION OF BIOLOGICAL FLUID COMPONENTS

(71) Applicants: Dominik Olbrzymek, Lodz (PL); Jakub Olbrzymek, Lodz (PL)

(72) Inventors: Bogdan Walkowiak, Strykow (PL); Malgorzata Siatkowska, Lodz (PL); Witold Szymanski, Lodz (PL); Piotr Komorowski, Lodz (PL); Leszek Olbrzymek, Lodz (PL); Dominik Olbrzymek, Lodz (PL); Jakub Olbrzymek, Lodz (PL)

(73) Assignees: Dominik Olbrzymek, Lodz (PL); Jakub Olbrzymek, Lodz (PL)

( * ) Notice: Subject to any disclaimer, the term of this patent is extended or adjusted under 35 U.S.C. 154(b) by 290 days.

(21) Appl. No.: 15/773,173

(22) PCT Filed: Oct. 31, 2016

(86) PCT No.: PCT/EP2016/076242
§ 371 (c)(1),
(2) Date: May 3, 2018

(87) PCT Pub. No.: WO2017/076810
PCT Pub. Date: May 11, 2017

(65) Prior Publication Data
US 2018/0326413 A1 Nov. 15, 2018

(30) Foreign Application Priority Data
Nov. 5, 2015 (EP) .................................... 15461575

(51) Int. Cl.
*B01L 3/00* (2006.01)
*G01N 33/49* (2006.01)
(Continued)

(52) U.S. Cl.
CPC .......... *B01L 3/5021* (2013.01); *G01N 33/491* (2013.01); *A01N 1/02* (2013.01);
(Continued)

(58) Field of Classification Search
CPC ............. B01L 3/5021; B01L 2200/028; B01L 2400/0633; B01L 2300/049;
(Continued)

(56) References Cited

U.S. PATENT DOCUMENTS 8,950,586 B2 * 2/2015 Dorian ................ A61M 1/3693
210/361
2002/0182718 A1 * 12/2002 Malmquist .............. B01L 3/563
435/287.2
(Continued)

FOREIGN PATENT DOCUMENTS

EP 2407245 1/2012
WO 2010115190 10/2010

*Primary Examiner* — Benjamin R Whatley
*Assistant Examiner* — Curtis A Thompson
(74) *Attorney, Agent, or Firm* — Mark M. Friedman

(57) ABSTRACT

A kit for centrifugal isolation of a fraction of interest from a multi-component composition according to density, comprising: a separation chamber (200) having an inlet (210) for introducing the multi-component composition and a base through-hole (220); characterized in that the separation chamber (200) comprises: an inlet section (211) communicating with the inlet (210), a base section (212) communicating with the base through-hole (220), wherein the inlet section (211) and the base section (212) communicate with each other via a necked duct (230) for detaching the inlet section (211) and the base section (212) at the necked duct
(Continued)

(230), wherein the separation chamber (200) has a form of a syringe in which the inlet of the separation chamber (200) is connectable with an extension nozzle or needle (215) for drawing the multi-component composition, and wherein the kit further comprises a plunger (240) for embedding and being slidably moved within the base section (212) of the separation chamber (200), wherein the plunger (240) comprises a plunger handle (242), removably attached to a plunger base (241), for sealing the base through-hole (220), and wherein the diameter of the necked duct (230) lumen is selected so as to maintain the multi-component composition, after detaching the inlet section (211) and the base section (212) at the necked duct (230), in the inlet section (211), by virtue of a partial negative pressure created within the inlet section (211) when the inlet (210) is sealed.

8 Claims, 9 Drawing Sheets

(51) Int. Cl.

| | |
|---|---|
| *B01D 17/12* | (2006.01) |
| *B01D 21/26* | (2006.01) |
| *B01J 19/00* | (2006.01) |
| *G03C 1/72* | (2006.01) |
| *A61M 1/36* | (2006.01) |
| *A01N 1/02* | (2006.01) |
| *C12M 1/34* | (2006.01) |
| *C12N 15/10* | (2006.01) |
| *A61J 1/20* | (2006.01) |
| *B04B 5/04* | (2006.01) |

(52) U.S. Cl.

CPC .................. *A61J 1/20* (2013.01); *A61M 1/36* (2013.01); *B01D 17/12* (2013.01); *B01D 21/26* (2013.01); *B01J 19/00* (2013.01); *B01L 2200/026* (2013.01); *B01L 2200/028* (2013.01); *B01L 2200/0631* (2013.01); *B01L 2300/042* (2013.01); *B01L 2300/049* (2013.01); *B01L 2300/0832* (2013.01); *B01L 2400/0409* (2013.01); *B01L 2400/0478* (2013.01); *B01L 2400/0633* (2013.01); *B04B 5/0442* (2013.01); *C12M 1/34* (2013.01); *C12N 15/10* (2013.01); *G03C 1/72* (2013.01)

(58) Field of Classification Search

CPC ....... B01L 2200/026; B01L 2400/0409; B01L 2400/0478; G01N 33/491; G03C 1/72; B01D 21/26; B01D 17/12; B01J 19/00; A61J 1/20; B04B 5/0442

See application file for complete search history.

(56) References Cited

U.S. PATENT DOCUMENTS

| | | | | |
|---|---|---|---|---|
| 2005/0123895 | A1 | 6/2005 | Freund | |
| 2006/0029923 | A1* | 2/2006 | Togawa ................. | B01D 61/18 435/2 |
| 2008/0166421 | A1* | 7/2008 | Buhr ...................... | A61K 35/18 424/530 |
| 2011/0083978 | A1* | 4/2011 | Lavi ................. | A61B 5/150755 206/223 |
| 2012/0053041 | A1 | 3/2012 | Ihm et al. | |
| 2014/0272925 | A1* | 9/2014 | Menon ................. | G01N 33/491 435/2 |
| 2015/0064687 | A1* | 3/2015 | Nemirovsky ......... | A61M 1/029 435/2 |
| 2015/0122713 | A1* | 5/2015 | Wu ...................... | B01L 3/5021 210/136 |
| 2015/0151035 | A1* | 6/2015 | Huemer .................. | B01L 3/502 210/321.6 |
| 2015/0209502 | A1* | 7/2015 | Bare ................ | A61B 5/150244 604/506 |
| 2015/0289856 | A1* | 10/2015 | Saqi ........................ | B01L 3/502 422/534 |
| 2016/0003712 | A1* | 1/2016 | Centeno ............... | B01D 21/262 494/37 |
| 2016/0367982 | A1* | 12/2016 | Pennie .................. | B01L 3/5021 |
| 2017/0059550 | A1* | 3/2017 | Bokka Srinivasa Rao .................. | B01L 3/5023 |

* cited by examiner

Stage 713  Stage 714  Stage 715  Stage 716  Stage 717

Stage 718  Stage 719  Stage 720

KIT FOR CENTRIFUGAL SEPARATION OF BIOLOGICAL FLUID COMPONENTS AND A METHOD FOR CENTRIFUGAL SEPARATION OF BIOLOGICAL FLUID COMPONENTS

TECHNICAL FIELD

The present invention relates to a kit for centrifugal separation of biological fluid components, such as blood components, and a method for centrifugal separation of biological fluid components.

BACKGROUND

Biological fluids, such as blood, lymph or urine include a variety of different component fractions. For example, whole blood includes plasma, blood platelets, red blood cells (RBC), white blood cells (WBC). Platelet rich plasma (PRP) and platelet poor plasma (PPP) can be obtained as a result of blood fractionation by centrifugation. By soft centrifugation PRP and other components can be obtained, whereas by strong centrifugation PPP and other components can be obtained. PRP can be converted to PPP by depleting of blood platelets by various methods (gel filtration, filtration, centrifugation, etc.).

Cell-free fractions of whole blood, i.e. blood serum and platelet poor plasma (PPP), are used in blood tests performed for clinical diagnosis and disease monitoring purposes. Moreover, well separated PRP can be used for aesthetic medicine purposes: PRP injected into specific areas of the skin can act as a matrix that promotes collagen to grow, and thus regenerates the tissue.

The process of separation of fraction of interest from the body fluid, such as separation of PRP from the blood, requires centrifugation performed on a centrifugal device. In order to separate a particular fraction from the body fluid, it is common to draw the fluid from the body into an evacuated tube, such as a syringe, that contains an appropriate amount of anticoagulant. The drawn blood is then subjected to fractionation, usually by differential centrifugation in centrifugal tubes. The tubes can contain additional separating substance (liquid or gel) helping the fractionation process.

In order to minimize the risk of infection by the blood sample, it is important to limit the steps of moving the blood sample from one vessel to another vessel during the separation procedure. Various research has been performed on the design of separation kits in order to facilitate drawing the fluid from the body and separating of particular fraction, as well as removing the separated component of interest.

A European patent application EP2407245 describes a centrifugal separation kit used for centrifugally separating blood into components. The kit comprises an injector acting as a syringe and a separation tube, in the form of a vial, filled with a cell isolation gel and having an open upper portion closable by a cap. The separation tube is further provided with a collecting unit located inside the tube and shaped so that it enables for installing the injector into the separation tube. The separation method involves collecting a whole blood by using the injector, removing a piston and a needle from the injector, installing the injector into the centrifugal tube, loading the set: injector-separation tube onto the centrifuge and operating the centrifuge to collect blood plasma components into the injector. After centrifugation, the blood plasma present in the injector is separated from the rest of blood components by uninstalling the injector from the separating tube. Nonetheless, simple construction of the kit requires the blood to contact with two vessels—the syringe and the separation tube, during centrifugation, which may increase the risk of infection by the drawn sample.

Another kit for centrifugal separation of the whole blood is known from the international patent application WO2010/115190. The kit comprises a syringe provided with a separation chamber, a syringe plunger, a port for installing a needle, a buoy guide post and two buoys fixedly mounted to the buoy guide post and slidably mounted within the separation chamber. The method for centrifugation involves drawing the whole blood directly from the patient into the separation chamber through the port of the separation chamber into the area between the second buoy and the plunger, rotating the chamber in a centrifuge so that the buoys bodies space apart, separating the blood component and removing separated blood components by depressing the syringe piston. Described therein, the syringe serves as both, a body fluid sampling device and a centrifugation tube. Nonetheless, the syringe has a multi-element structure which may further lead to increase the costs of production, thus, increasing the price of the kit.

A US patent application US2012/053041 describes a kit for centrifugally separating whole blood into factions: RBC, PPP and PRP. The kit comprises an injector in a form of syringe and a centrifugal separation tube provided with the support formed within upper portion of the tube. In order to separate the whole blood into fractions, the syringe is used to draw the whole blood, and then the syringe, filled with the blood, is tightly installed in the support formed in the upper portion of the centrifugal separation tube. Subsequently, the kit (i.e. the tube with the installed injector) is loaded into the centrifugal separator. The centrifugation process provides separation of the whole blood into fractions, wherein blood plasma components, i.e.: PPP and PRP fractions are present within the injector cylinder. Isolation of the blood plasma components is accomplished by pulling the syringe out of the centrifugal separation tube Nonetheless, during centrifugation of the kit, due to the strong centrifugal force acting on the kit, the injector may jam within the centrifugal separation tube, thereby precluding the kit detachment as well as separation of the PPP fraction present in the injector cylinder. Moreover, the performed operations of drawing and centrifuging require the drawn blood to be contacted with at least two physically separated containers, i.e. the injector and the centrifugal separation tube. This affects sterility of the blood during the centrifugation process and increases the risk of the blood contamination, since each container has to be separately sterilized, packed and stored. Furthermore, the operator of the syringe-vial kit is more prone to infection with the pathogens present in the blood sample, as the operation with the multi-containers kit requires experience and precision. Thus, the operation with the kit may cause undesirable contact of the blood sample and the operator body by the direct contact either with the syringe or the vial.

A US patent application US2015/122713 describes a device for separating platelet rich plasma (PRP) from whole blood, using a process involving vibrations or oscillations. The device comprises a base container and an upper container. The containers are rotatably (pivotably) connected to each other by a narrowed neck comprising, in its interior, two parallel plates—each with two apertures, wherein each plate is fixedly mounted to the orifice of one container. Thus, when the aperture of the corresponding plates overlap, the blood, introduced into either container, can freely flow from one container to another, through the overlapping apertures of the narrowed neck. Following the vibration/oscillation separation process, the base container and the upper container are rotated relative to each other, in order to offset (separate) the apertures of the corresponding plates in the narrowed neck. Subsequently, the desired blood fraction is drawn from the appropriate container of the separating device by using a syringe. Therefore, the narrowed neck does not enable the containers to be detached, but it only enables for separation of the containers interiors, whilst the containers are physically connected. Moreover, the construction of the separating device is configured for separation by vibration or oscillation, and not centrifugation. The vibration/oscillation separation process of the bodily fluid requires different construction of the separating devices from the construction of the devices that are configured to be used in centrifugal separation processes, due to different forces acting on the device during separation.

A US patent application US2005/0123895 describes a kit for centrifugal separation of bodily tissues and collection of the fat. The system comprises a centrifuge, syringe and an adapter. The separation method involves drawing of the tissue into the syringe chamber, detaching the syringe piston and inserting the syringe in a centrifuge. Subsequently the syringe, serving as a centrifugal tube, is centrifuged. The lower end of the syringe is configured to accept the adapter that is used during removal of denser substrates from the syringe, after the centrifugation process. The adapter is also used for transferring fat cells or fat tissue into smaller syringes. Thus, in US2005/0123895, the syringe cylinder is used for centrifugation, but the centrifuged fractions are removed from the syringe, into smaller syringes (constituting another chambers), by means of the adapter, if mounted to the syringe. These affects the sterility of the obtained tissue components since the desired centrifuged fraction, i.e. the fat, has to be transferred into another container, in order to be isolated and stored.

There is a need for further development of the kit construction for centrifugal separation of biological fluids, including: blood, lymph or urine, according to the components density that will simplify the kit construction as well as reduce the number of vessels required to be in contact with the composition to be separated.

SUMMARY

There is disclosed a kit for centrifugal isolation of a fraction of interest from a multi-component composition according to density, comprising: a separation chamber having an inlet for introducing the multi-component composition and a base through-hole; characterized in that the separation chamber comprises: an inlet section communicating with the inlet; a base section communicating with the base through-hole; wherein the inlet section and the base section communicate with each other via a necked duct for detaching the inlet section and the base section at the necked duct; wherein the separation chamber has a form of a syringe in which the inlet of the separation chamber is connectable with an extension nozzle or needle for drawing the multi-component composition; and wherein the kit further comprises a plunger for embedding and being slidably moved within the base section of the separation chamber, wherein the plunger comprises a plunger handle, removably attached to a plunger base, for sealing the base through-hole; and wherein the diameter of the necked duct lumen is selected so as to maintain the multi-component composition, after detaching the inlet section and the base section at the necked duct, in the inlet section, by virtue of a partial negative pressure created within the inlet section when the inlet is sealed.

The separation chamber may further comprise a housing surrounding the necked duct at the exterior of the separation chamber.

The inlet may comprise means for temporarily sealing the inlet.

The necked duct can be configured to be detached by breaking or cutting or screwing.

The kit may further comprise a centrifugal tube comprising a closed bottom and an opening configured for introduction of the separation chamber into the centrifugal tube by facing the base through-hole and the bottom of the centrifugal tube.

The centrifugal tube may comprise a cover for covering the opening of centrifugal tube and the inlet of the separation chamber, wherein the cover is configured so as to independently seal the inlet of the separation chamber and the opening of the centrifugal tube.

There is also disclosed a method for centrifugal separation of a fraction of interest from a multi-component composition according to density by using the kit as described herein, the method characterized in that it comprises the steps of: sealing the base through-hole of the separation chamber if not yet sealed; loading the multi-component composition into the separation chamber through the inlet; sealing the inlet and exposing the base through-hole; introducing a separator into the separation chamber via the base through-hole; centrifugation of the separation chamber at unsealed inlet; sealing the inlet; and detaching the inlet section and the base section of the separation chamber at the necked duct.

The method may comprise introducing the multi-component composition into the separation chamber provided with a plunger embedded within the base section of the separation chamber and creating at least partial vacuum within the separation chamber.

The method may comprise exposing the base through hole by removing of the plunger handle from the plunger base.

The method may comprise removing the housing from the separation chamber after centrifugation, and prior to detaching the separation chamber at the necked duct.

BRIEF DESCRIPTION OF THE DRAWINGS

The object of the invention is presented by means of exemplary embodiments in a drawing, in which.

DETAILED DESCRIPTION

The kit according to the invention is configured to separate the fraction of interest from the body fluid according to the fraction density by means of a centrifuge. Exemplary body fluids which can be processed with the kit are blood, lymph, urine, wherein the fraction of interest (i.e. the target substance) is a fraction of particular density. For example, when the multi-component composition is whole blood—the platelet rich plasma (PRP) may be the target substance to be centrifugally separated using the kit.

The kit comprises a separation chamber, which may have the form of a container having a suitable size or shape. For example, the separation chamber may be substantially longitudinal, and preferably cylindrical. The kit may further comprise a centrifugal tube (e.g. 150 in FIG. 1C) to be used in combination with the separation chamber during centrifugation, or the separation chamber may be configured to be centrifuged without using the centrifugal tube.

Figure 1C:
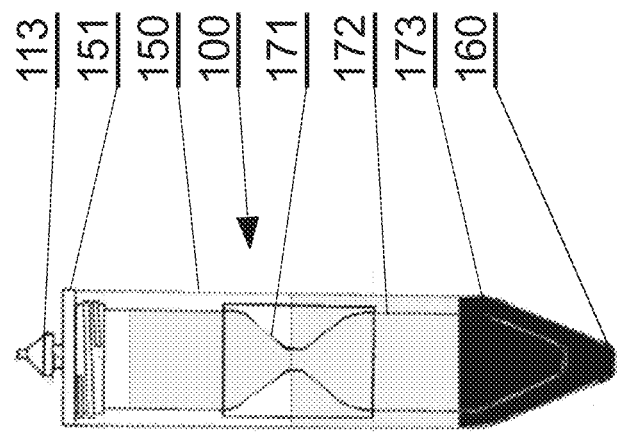
FIGS. 1A-1C present a schematic view of the separation chamber according to a first embodiment.
Figure 1B:
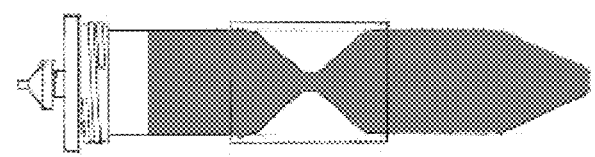
Figure 1A:
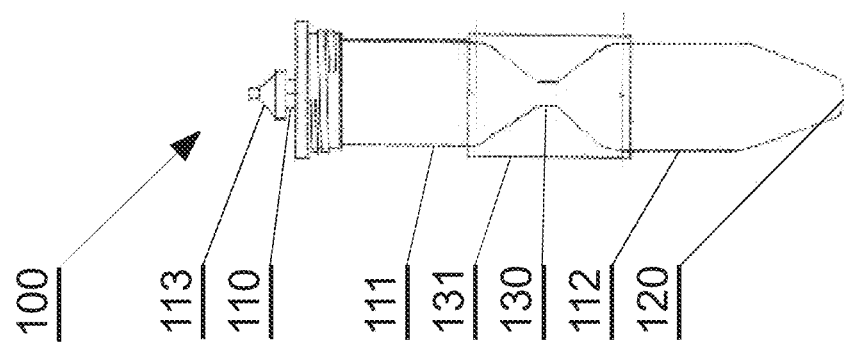

FIG. 1A shows the separation chamber 100 according to the first embodiment of the invention, and FIG. 1B shows the separation chamber 100 filled with body fluid. The separation chamber 100 serves as a vial for centrifugation of the body fluid introduced into the chamber 100. The separation chamber 100 comprises an inlet 110 for introducing the body fluid into the interior of the chamber 100 and a base through-hole 120 located substantially opposite to the inlet 110, so that the inlet is formed in the upper part of the chamber 100, whilst the base through-hole is formed in the base part of the chamber 100. The inlet 110 and the base through-hole 120 are configured to be temporarily sealed, e.g. by means of a suitable cover, such as a cap, a stopper, or a closable valve. The separation chamber 100 further comprises a necked duct 130 formed within the chamber 100. The necked duct 130 divides the interior of the separation chamber 100 into an inlet section 111 and a base section 112, as well as it serves as a passage for the body fluid introduced into the separation chamber 100, so that once introduced fluid, e.g. drawn blood, can freely flow from the inlet section 111 to the base section 112 through the necked duct 130 due to the force of gravity.

The interiors of the sections 111, 112 communicate one with each other via the necked duct 130 so that the sections 111, 112 constitute a system of connected vessels, wherein the inlet section is provided within an inlet portion of the separation chamber 100 and communicates directly with the inlet 110 and the base section 112, whilst the base section 112 communicates directly with the base through-hole 120 and the inlet section 111.

Figure 2:
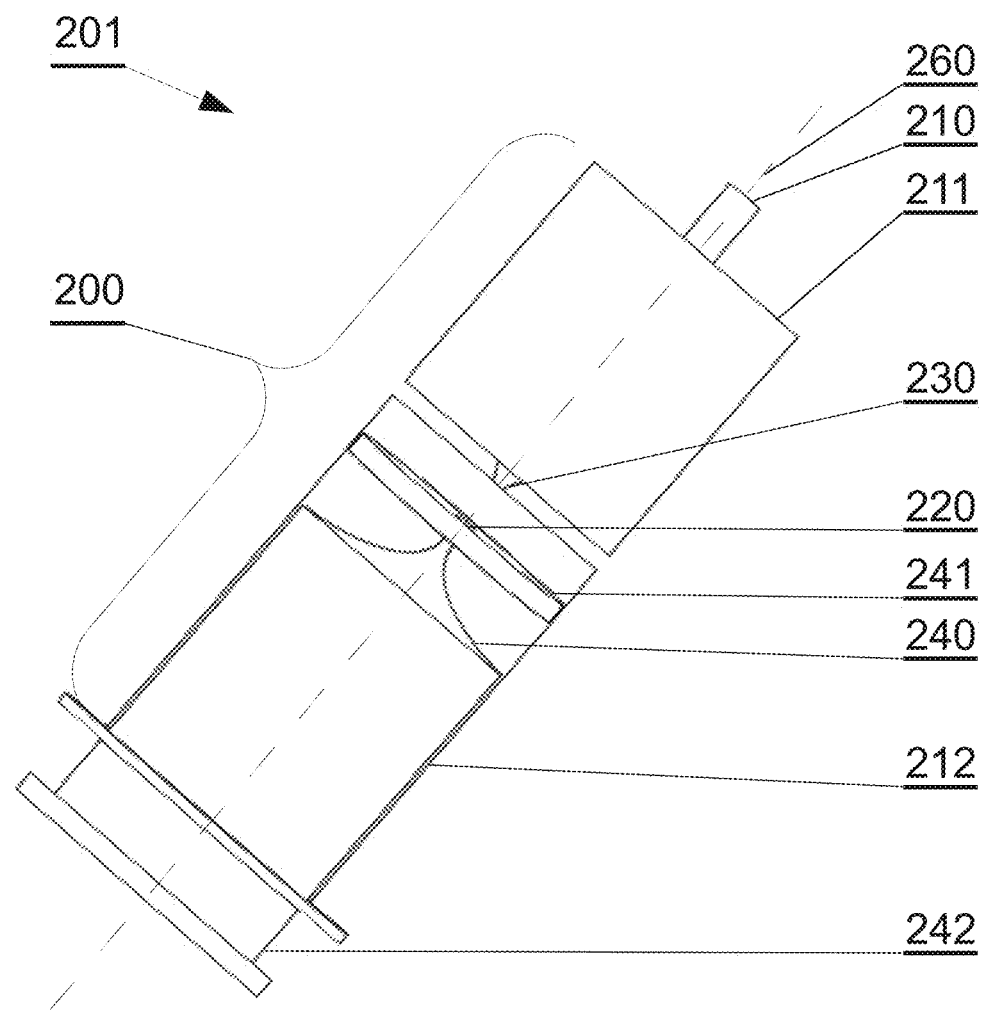
FIG. 2 presents a schematic view of the separation chamber according to a second embodiment.

The necked duct 130 facilitates detaching the inlet chamber 111 and the base chamber 112 at the necked duct 130 (preferably, after centrifugation of the chamber 100 with the body fluid). Therefore, the necked duct 130 enables for physical separation of the separation chamber 100 into the inlet section 111 and the base section 112. The necked duct 130 can have any suitable form, e.g. a form of neck formed at the sidewall of the separation chamber 100 (as shown in FIG. 1) or may constitute a rigid or flexible, substantially straight conduit 230—as shown in FIG. 2. Nonetheless, depending on the specific needs, the necked duct 130, 230 may be of a more complex construction, for instance of a screw-type so that the inlet and the base sections 111, 112 may be re-connected by screwing, e.g. to re-use the separation chamber 100, preferably after suitable sterilization (not shown).

Depending on the construction of the necked duct 130, detachment of the inlet and base sections 111, 112 may be accomplished, for example, by breaking or by cutting the necked duct 130, 230 in an irreversible manner.

Figure 3A:
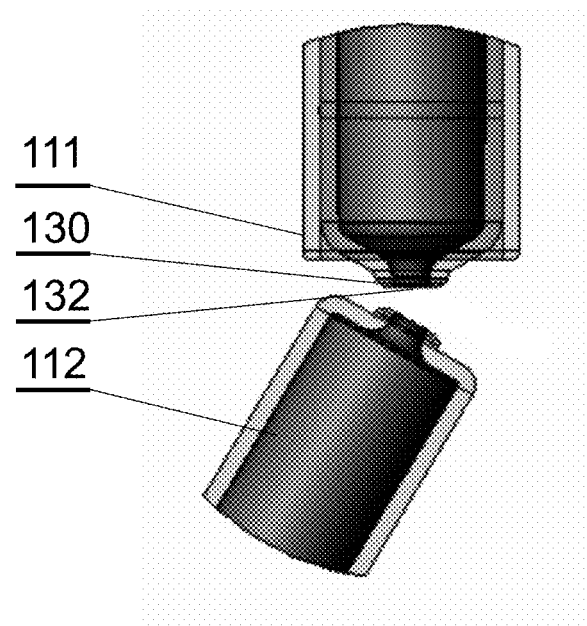
FIG. 3A presents a schematic view of the broken necked duct of the separation chamber in the embodiments of FIGS. 1A-C and 2.

FIG. 3A shows a broken necked duct 130 in enlargement. Detaching of the separation chamber at the necked duct 130 exposes a duct lumen 132, whilst the inlet section 111 and the base section 112 are physically disconnected.

As shown in FIG. 1, the necked duct 130 may be further provided with a housing 131 e.g. of cylindrical shape that externally surrounds the necked duct 130 and prevents from detaching of the duct 130 during operation of the separation chamber 100, e.g. during centrifugation process.

As shown in FIG. 3A, the diameter of the duct lumen 132 is selected so as to maintain the liquid in inlet section 111 by virtue of partial negative pressure created when the inlet 110 is sealed, and the separation chamber 100, filled with liquid, is detached at the necked duct 130 (i.e. where the lumen 132 of the duct is exposed).

The inlet 110 of the separation chamber may be in a form of different suitable inlet, e.g. in a form of conduit or a passage that permits the body fluid to enter the separation chamber 110; the inlet 110 is suitable for being temporarily sealed and may be provided with a cover or valve. FIG. 1C shows an exemplary inlet cover 113 in a form of small stopper for temporarily sealing the inlet 110.

The base through-hole 120 of the separation chamber 100 has a construction that allows for temporarily sealing the base through-hole 120, e.g. by a suitable cover or cap or stopper or the base through-hole may be provided with a closable valve (not shown in FIG. 1). Preferably, the diameter of the base through-hole 120 is selected so as to maintain the liquid in the separation chamber 100 at the sealed inlet 110 by virtue of partially negative pressure created within the chamber 100.

As shown in FIG. 2, the base section 212 of separation chamber 200 may be further configured so as to provide embedding of a plunger 240 within the base section 212 of separation chamber 200. For example, the base section can have a form of a cylinder with an opening formed in the base so that the plunger 240 can slidably enter the base section 212, thus forming a syringe 201. The separation chamber 200 (provided with the plunger 240) in a form of syringe 201 is suitable for collecting the fluid directly from a patient body, because the plunger 240 may facilitate drawing of the body fluid into the separation chamber 200 by creating at least partial vacuum.

The plunger 240 comprises: a plunger base 241 for separating the interior of the base section 212 from the exterior of the separation chamber 200 and a plunger handle 242 connected to the plunger base 241. The plunger 240 is configured to slidably move within the separation chamber 200 along the longitudinal axis of the syringe 260, wherein the movement of the plunger is restricted to the second segment 212 of the separation chamber due to necked duct 230, which forms a narrowing in the inner diameter of the separation chamber 200. Preferably, the plunger handle 242 may extend over the exterior of the base section 212 to facilitate operation of collecting of the patient fluid into the separation chamber 200. The plunger base 241 has an opening, formed through the base 241 of the plunger 240, which constitute a base through-hole 220 of the separation chamber 200. The handle of the plunger 242 is removably attached to the plunger base 241, so as to seal the base through-hole 220 when operating of the syringe and to expose the base through-hole 220 after collecting of the biological fluid in the separation chamber 200 by removing the plunger handle 242.

Figure 3B:
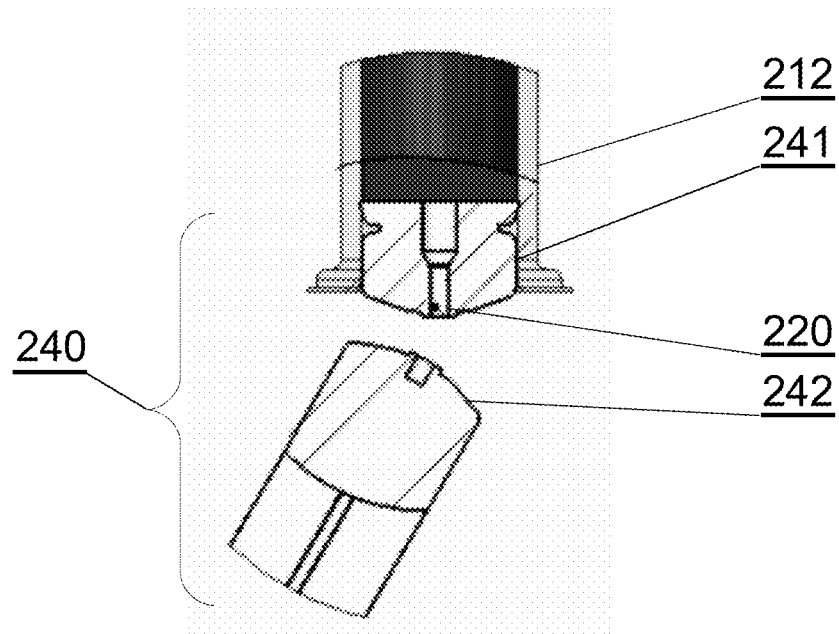
FIG. 3B presents a schematic view of the detached plunger handle and the plunger base in the embodiment of FIG. 2.

The handle 242 may be connected to the base 241 in any suitable manner that permits removal of the handle from the base, so that the base stays present in the base section 212 of the separation chamber 200 during and after removal of the handle 242, whilst the handle removal exposes the base through-hole 220. For instance, the plunger handle 242 may be connected with the base 241 via the necking of the material formed at the connection of the base 241 and the handle 242—as shown in FIG. 2 and FIG. 3B, or the handle 242 may be screwed to the base 241. The base-handle connection of screw-type (not shown in the drawing) provides the plunger to be re-used, preferably after suitable disinfection.

Depending on the connection type, removing of the handle 242 from the base 241 may be accomplished, for example, by breaking or cutting of the handle 242 at the base 241. FIG. 3B shows the plunger base 241 remaining within the separation chamber whilst the base through-hole 220 is exposed, i.e. after breaking of the plunger handle 242 at the base 241.

Figure 4:
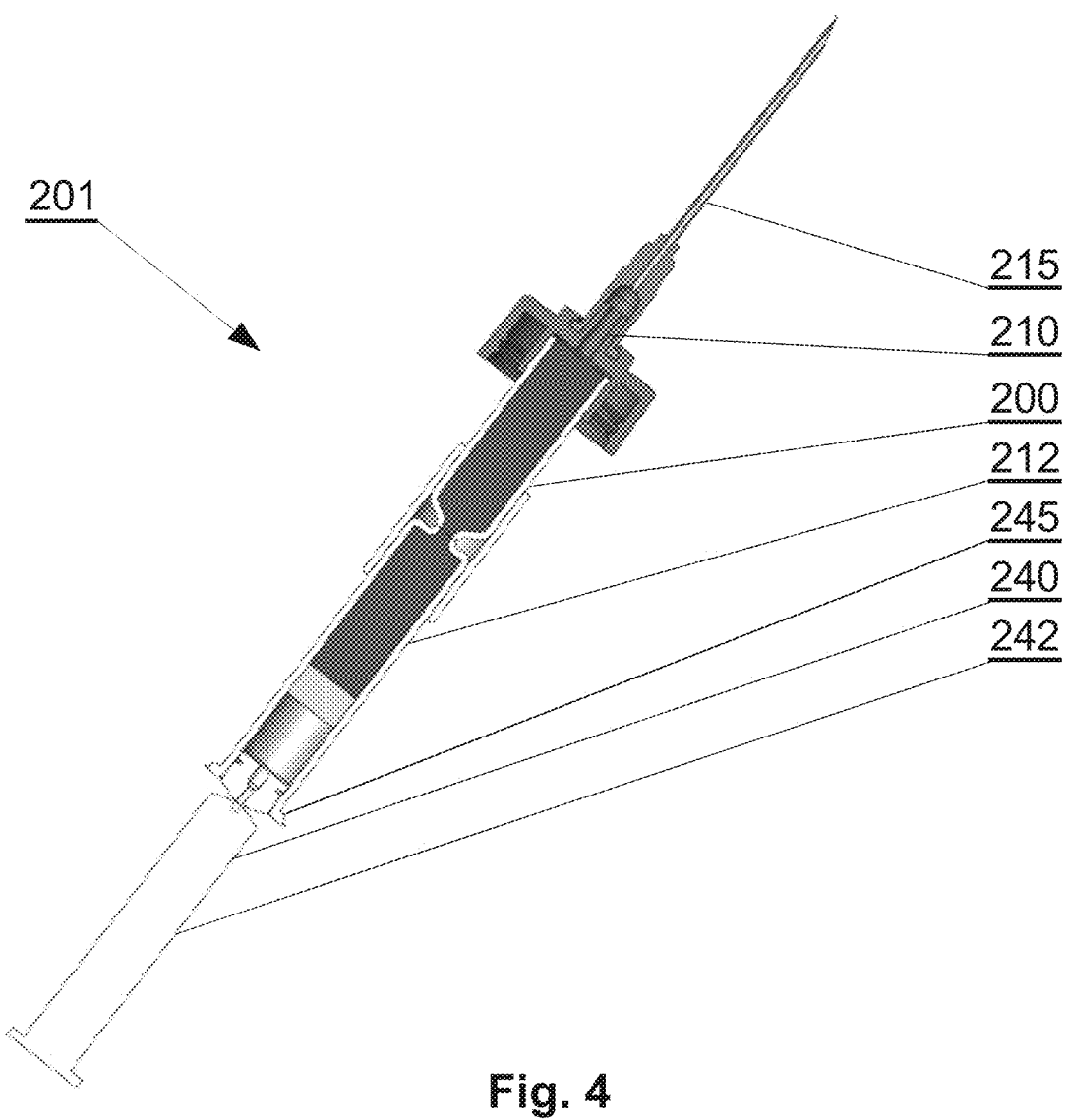
FIG. 4 presents a schematic view of the loaded syringe with installed needle.

In order to facilitate collection of the body fluid, the inlet 210 of the separation chamber may be configured so as to be connected with extension nozzle such as a needle 215. FIG. 4 shows a syringe 201 comprising a separation chamber 200 with collected blood and retracted plunger 240 closing the bottom of the separation chamber 200. The needle 215 mounted on the inlet 210 of the separation chamber may facilitate collection of the body fluid, e.g. directly from the patient body.

Figure 5B:
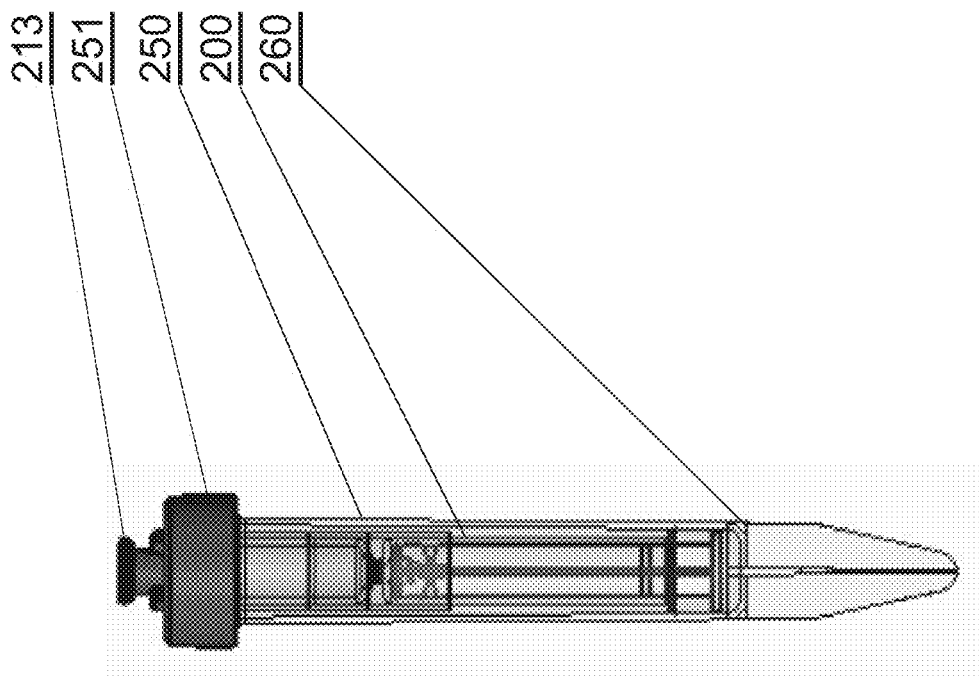
FIG. 5B presents a schematic view of the kit comprising the syringe loaded into the centrifugal tube.
Figure 5A:
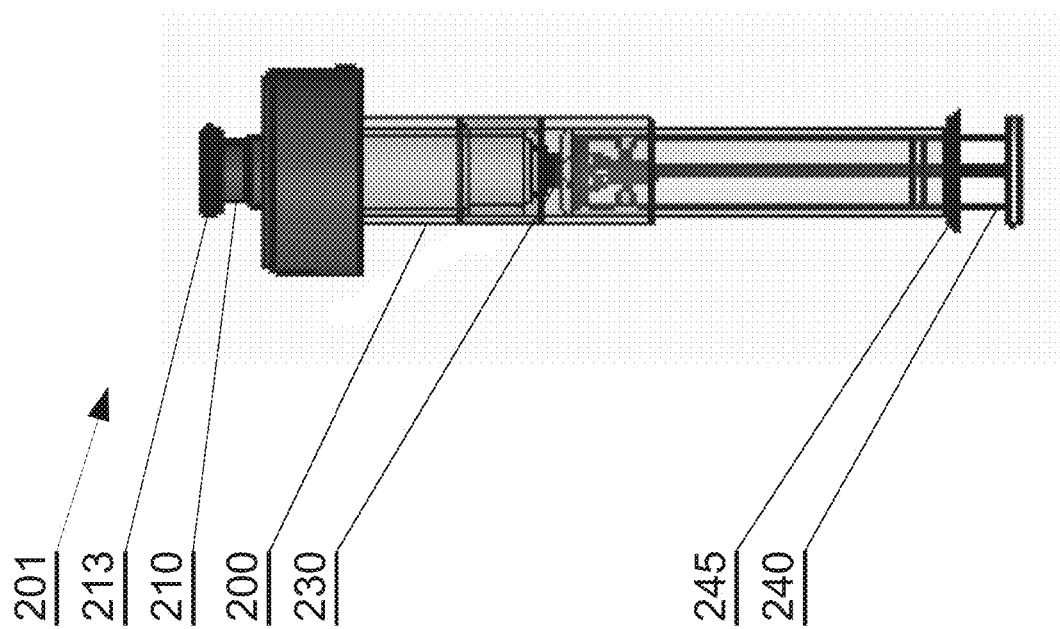
FIG. 5A presents a schematic view of the empty syringe covered with a cap.

FIG. 5A shows a syringe 201 with a plunger 240 loaded into the base section of the separation chamber 200. The inlet 210 of the separation chamber 200 is sealed with a cover 213 which ensures that the drawn biological fluid remains inside the separation chamber while exposing of the base through-hole 220 (as shown at stage 705 in FIG. 7A). This is due to the negative pressure created in the separation chamber, which further leads the biological fluid to be retained either in the separation chamber or (as, for example, after centrifugation process) in the inlet section of separation chamber whilst the separation chamber is detached at the necked duct 230 into the inlet section and the base section.

The kit for separation of multi-component composition may further comprise a centrifugal tube provided with a closed bottom. FIGS. 1C and 5B show respectively a separation chamber 100, 200 loaded into a centrifugal tube 150, 250. The centrifugal tube may serve as a protection housing maintaining a separation chamber in sterile conditions during storage as well as preventing mechanical damages during centrifugation of the separation chamber. Nonetheless, the bottom through-hole 120, 220 (FIGS. 1A, 2) of the separation chamber may be covered with a different suitable cover for centrifugation—for centrifugation carried out without the centrifugal tube.

Moreover, the centrifugal tube 150, 250 may serve as means for introducing into the syringe a certain amount of a separator. Introduction of the separator may be accomplished by loading the separation chamber 100, 200 into the centrifugal tube 150, 250, respectively, so as to face the bottom through-hole of the separation chamber and the bottom 160, 260 of the centrifugal tube filled with separator.

The centrifugal tube 150, 250 may further comprise a cover 151, 251 for covering the opening of the tube, e.g. during storage of the separation chamber in the centrifugal tube or during centrifugation. The cover 151, 251 may be a separate cover, or it may be further configured so as to seal both the opening of the centrifugal tube and the inlet 110, 210 of the separation chamber, while the separation chamber 100, 200 is introduced into the centrifugal tube 150, 250 (FIG. 1C, 5B). For example, the cover 151, 251 of the centrifugal tube may be provided with an opening for exposing the inlet 110, 210 of the separation chamber, whilst the separation chamber is loaded into the centrifugal tube. In this case, the inlet 110, 210 may be provided with a separate cap 113, 213 to be opened or closed regardless of the centrifugal tube 150, 250 being open. The cover 151. 251 of the centrifugal tube may be further configured to prevent the separation chamber from moving within the centrifugal tube. It can be accomplished by fixedly attaching the cover 151, 251 to the separation chamber 100, 200 over the inlet area 110, 210 of the separation chamber whilst the cover edge overlaps the opening of the centrifugal tube and provides a threaded connection between the cover and the centrifugal tube, so that the cover may be threaded to the opening of centrifugal tube.

Figure 6:
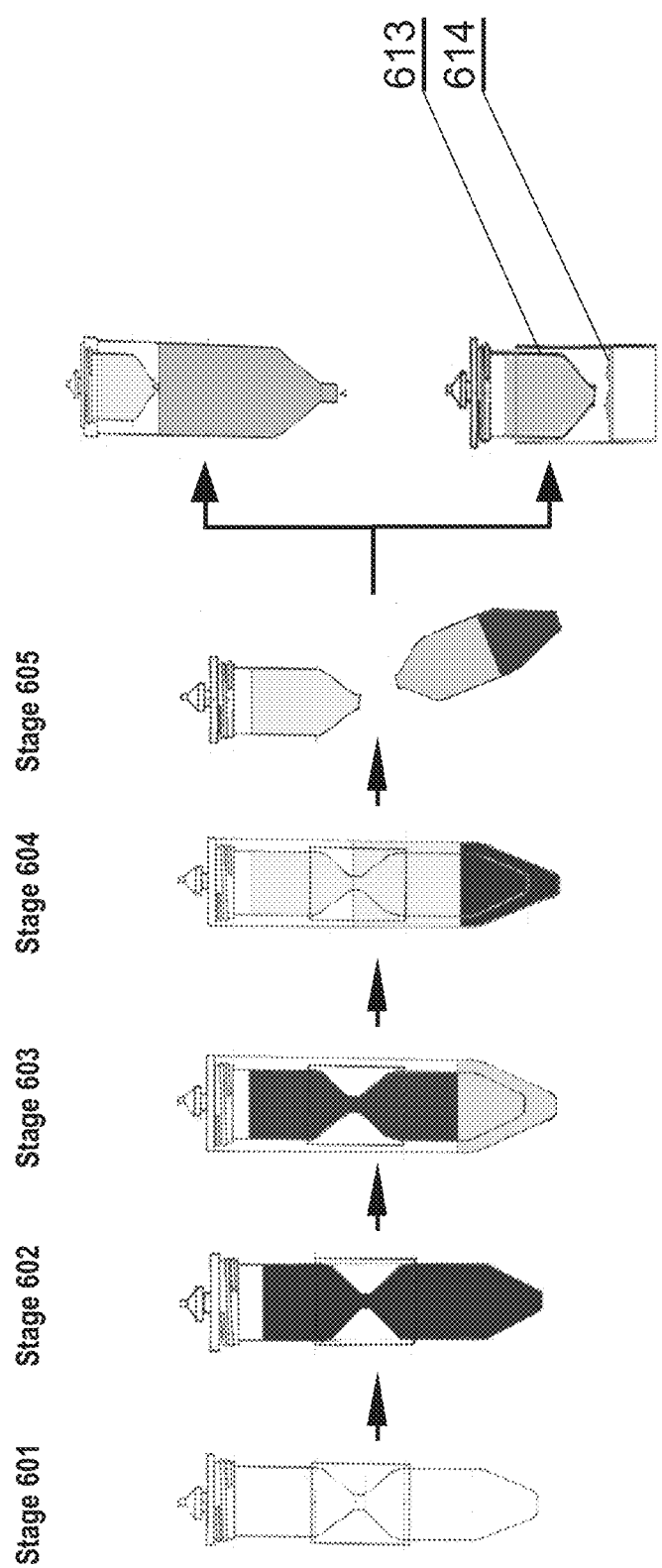
FIG. 6 presents illustrative views of various stages in the method for centrifugal separation of biological fluid by using the kit comprising the separation chamber according to the first embodiment.

As shown in FIGS. 4, 5A and 5B, the plunger 240 may be further provided with a sealing 245 attached to the edge of the plunger base 241 so as to prevent collected biological fluid from leaking from the base section of separation chamber. The separator shall be free to flow between the walls of the chamber 200 and the centrifugal tube 250 which are connected as communicating vessels via the inlet 210. FIGS. 6 and 7 illustratively show a method for separation a certain fraction of biological fluid by means of the kit described above.

The method involves the following steps:
- sealing the base through-hole 120, 220 of the separation chamber 100, 200 if not yet sealed;
- loading the biological fluid to be separated into the separation chamber 100, 200, through the inlet 110, 210;
- sealing the inlet 110, 210 and exposing the base through-hole 120, 220;
- introducing a separator into the separation chamber 100, 200 via the base through-hole 120, 220;
- centrifugation of separation chamber with unsealed inlet 110, 210;
- sealing the inlet 110, 210 and the base through-hole 120, 220 after centrifugation;
- isolating the fraction of interest by detaching the inlet section 111, 211 and the base section 112, 212 of the separation chamber at the necked duct 130, 230 at a closed inlet 110, 210.

FIG. 6 shows schematically, by stages, the method for separating biological fluid by means of the kit comprising the separation chamber according to the first embodiment of the invention, whilst FIG. 7 schematically shows, by stages, the method for separating biological fluid by means of the kit comprising the separation chamber according to the second embodiment of the invention. The separation chamber 100, 200 may be equipped with a centrifugal tube 150, 250 serving as a housing that maintains separation chamber 100, 200 in sterile conditions and prevents mechanical damages.

The procedure may involve:
providing a separation chamber (stage 601, 701);
taking the syringe out of the centrifugal tube (stage 702);
filling the centrifugal tube 150 with a predetermined volume of separator of certain density (stage 703), e.g. cell separation liquid;
installing the needle onto the syringe port—if required (stage 704);
collecting the body fluid into separation chamber (stage 704, 602) at a sealed base through-hole;
uninstalling the needle—if it has been installed;
sealing the inlet (stage 705, 602) and exposing the base-through hole (stage 705, 602) e.g. by removing the plunger handle (stage 705) or by taking off a cover;
Following exposure of the base through-hole (stage 602, 705) e.g. by removal of the syringe handle, the separation chamber may be shaken (stage 707).

Assembling of the needle is required, for example, when the body fluid is drawn directly from the patient's body or from a vial having a narrow opening.

Moreover, when the composition to be separated is blood, the lumen 132 of the necked duct 130 of the separation chamber may be provided with anticoagulant. Restriction of the plunger movement to the second section of the separation chamber leads to introduction of the air into the syringe, when collecting of the biological fluid, as the air is present in the inlet section of separation chamber. This may further increase the mixing efficiency of the body fluid and anticoagulant.

Figure 7A:
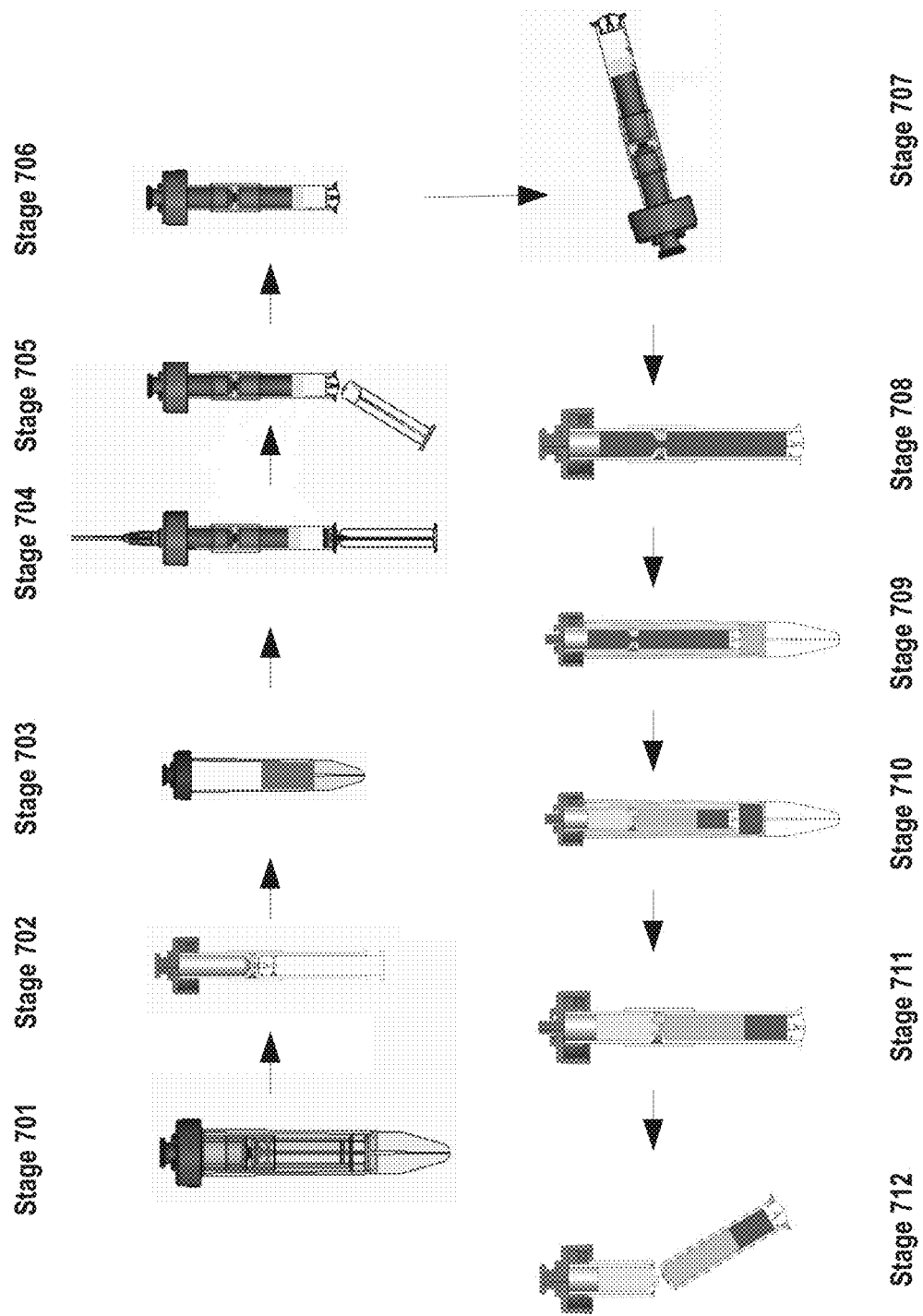
FIG. 7A presents illustrative views of various stages in the method for centrifugal separation of body fluid by using the kit comprising the separation chamber according to the second embodiment.
Figure 7B:
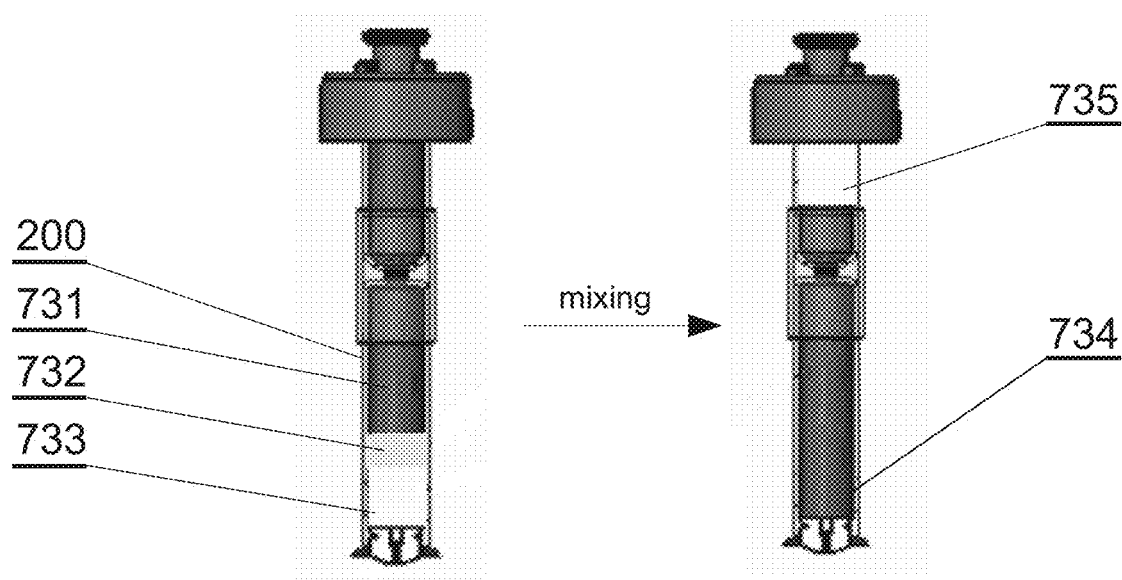
FIG. 7B presents an illustrative view of the result of the mixing process and movement of air upwards.

FIG. 7B shows in enlargement, the separation chamber 200 comprising drawn blood. Prior to mixing, the separation chamber 200 may comprise an uppermost layer of drawn blood 731, a middle layer of anticoagulant 732 and a lower layer of air 733 that was drawn from the first inlet section of the separation chamber whilst blood collection. Due to shaking of the separation chamber, the blood mixes with anticoagulant, and generated air bubbles go upstream, thereby increasing mixing turbulences, and thus, enhancing efficiency of mixing the blood and anticoagulant. As a result of the mixing process, the air constitutes the uppermost layer 735 above blood mixed with anticoagulant 734.

Following the mixing (stages 707, 708), the separator is introduced into the separation chamber via the bottom through-hole (stages 709, 603). Introduction of the separator may be accomplished by loading the separation chamber into a centrifugal tube filled with the separator so as to face the base through-hole with the bottom of the centrifugal tube with open inlet port (stages 709, 603). This causes immersion of the base through-hole within the separator, leading certain volume of the separator to flow into the separation chamber due to the removal of air from the top through open inlet port.

The centrifugal tube may be filled with different separators, having different density—depending on the density of fraction of biological fluid to be separated. For example, for isolation of PRP from blood, common cell separation liquid may be used, such as sucrose or commercially available Percoll® or Ficoll®.

Next, the separation chamber is loaded onto the centrifuge (stage 709, 603) in a vertical position, so that the inlet section of separation chamber is set above the base section. Due to centrifugation process the multi-component composition is separated into fractions according to density (stages 710, 604), whereupon the liquid separator flows into a position between the heavier and the lighter fraction by virtue of the relative densities. Referring to FIGS. 1A and 1C, the volume of the inlet and second section of the separation chamber may be engineered so that the lighter fraction 171 occupies the whole volume of the inlet section 111, whilst the separator 172 and the heavier fractions 173 occupy the base section 112 of the separation chamber 100, as well as part of the centrifuge tube, as shown in FIG. 1C and FIG. 7A. After centrifugation, the separator 172 is leaving a soft barrier between the fraction of interest 171 and other fractions 173.

The fraction of interest may be that of a lower density, i.e. located above the layer of the separator in the inlet section of the separation chamber (as shown in FIG. 1C). Alternatively, the fraction of interest may be that of greater density lying below the layer of separator in the bottom section.

For instance, due to centrifugation of whole blood, PRP may be isolated by using sucrose, Percoll® or Ficoll® as a separator. The volume of separated PRP fraction may be predetermined on the basis of the blood volume to be drawn, and thus, either the volume of the first (inlet) section may be adjusted to fit the PRP volume, or the blood volume to be drawn may be adjusted to fit the volume of the particular section of separation chamber.

Following centrifugation, the inlet 110, 210 of the separation chamber is sealed (stages 710, 804), the separation chamber is withdrawn from the centrifugal tube (stages 711, 605) the housing is removed from the necking (if present) (stages 711, 605) and the separation tube is detached at the necked duct (stages 712, 605) leading to isolation, separated by centrifugation, the fraction of interest from the other fractions of biological fluid. The lumen of the necked duct exposed by detaching of the separation chamber may be sealed by suitable cover, so that one of the sections of the separation chamber, filled with isolated fraction of interest, may be stored, e.g. until testing or using. Therefore, the isolated fraction of interest may be stored in the same container into which it was drawn and in which it was centrifuged. This provides improved safety of the whole process of collecting, centrifuging and storing of the biological fraction of interest since the whole multi-component composition as well as the isolated fraction of interest has direct contact only with one container and this considerably reduces the risk of contamination of the biological components of the isolated fraction.

Figure 7C:
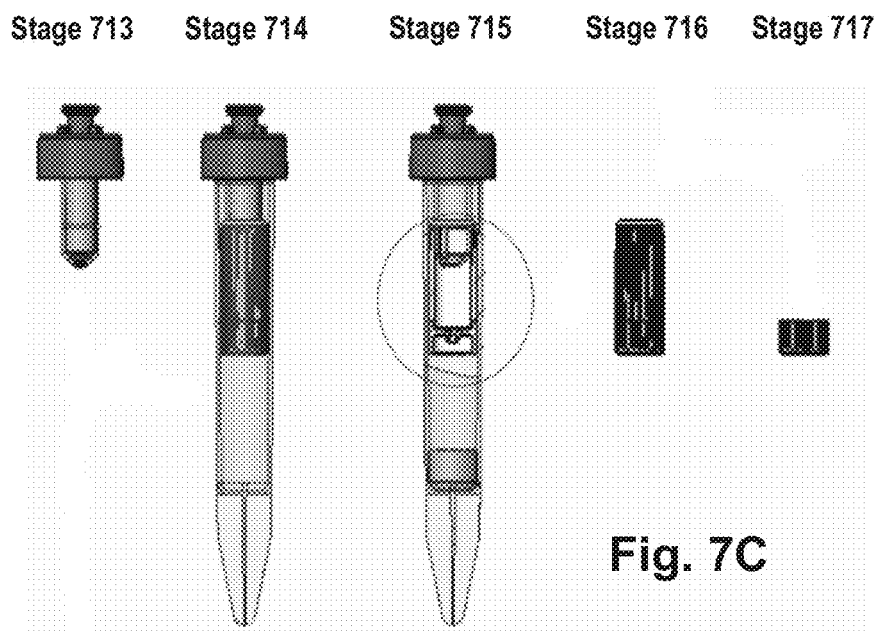
FIGS. 7C, 7D present an illustrative view of the method for filtration of isolated fraction of body fluid.

The isolated fraction (stages 712, 605) may be subjected to further treatment. FIGS. 6 and 7C schematically show a method for filtration of the isolated PRP by using the kit according to the invention. The method for filtration may be carried out by introducing the section of separation chamber filled with PRP (613, 713), onto the membrane filter that retains platelets on the membrane. The filter 614 may be any suitable filter, and the filtration method may involve typical filtration under normal pressure or can involve additional centrifugation or pressure gradient for more rapid filtration.

Optionally, the filter may comprise a two-part housing 716, 717 that holds the membrane filter, as well as maintains the section of separation chamber 713 within the centrifugal tube 714, as shown in FIG. 7C. The filtration process may involve mounting of the inlet section of the separation chamber 713, filled with PRP, onto the filter 714 and mounting the filter into centrifugal tube followed by centrifugation of PRP. The centrifugation provides separation of the platelets which retains on the filter membrane, whilst platelet poor plasma (PPP) collects onto the bottom of centrifugal tube 715.

Figure 7D:
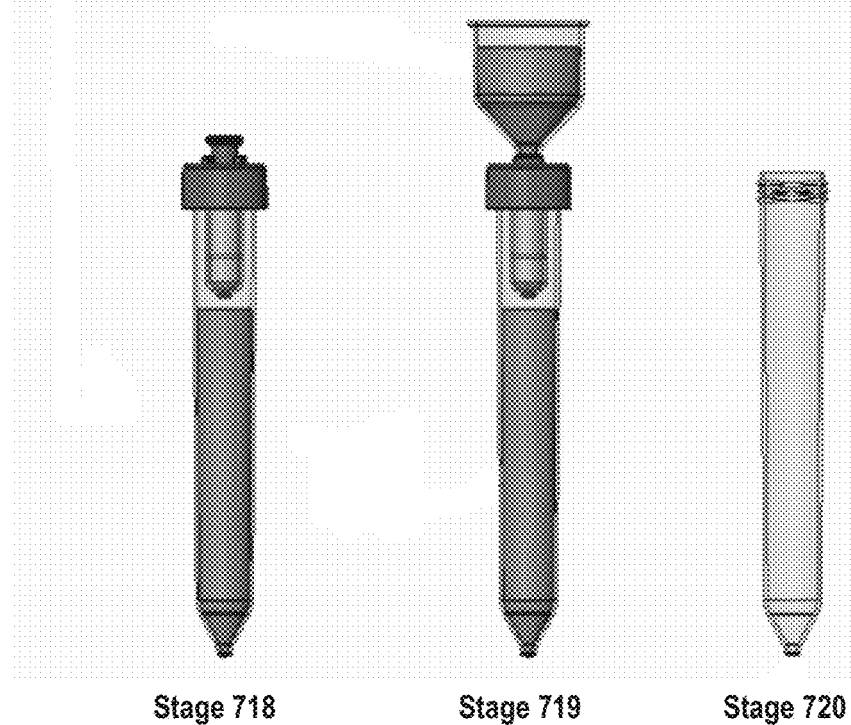

Moreover, filtration of the PRP may be carried out by using gel filtration technique, as show in FIGS. 6 and 7D. The method may involve: mounting the PRP in the first section of separation chamber onto the column filled with filtration gel, washing the PRP with a suitable buffer 603, 719 and collecting the washed platelets at the column outlet. The column outlet may be further provided with a strainer 720. Gel filtration provides separation of blood platelets from plasma proteins.

The kit according to the present invention provides separation of variety of biological fluids into fractions according to their density, as well as for easy isolation of the fraction of interest by detaching the separation chamber at the necked duct. The kit is suitable for isolation, e.g. of PRP from the whole blood drawn directly from the patient body, as well as for isolation of different components from multi-component compositions, such as lymph or urine. Moreover the kit may be used for separation of non-biological multi-component compositions where the density of fraction of interest is known or predictable, so as to adjust proper density of the separator.

One of the advantage of the kit is that the kit restricts the number of vials/containers to be in contact with the fraction of interest during and after isolation and separation procedure, thereby reducing the risk of contamination of the composition to be separated and infection with biohazard factors of the operator.

Moreover, construction of the separation chamber provides safety centrifugation process. Inlet section and base section constitutes one continuous separation chamber, which is configured to be detached after centrifugation process.

Moreover, the separation chamber may be provided with housing disposed around the necked duct to protect the duct from breaking the duct during centrifugation.

The invention claimed is:

1. A kit for use in centrifugal isolation of a fraction of interest from a multi-component composition according to density, the kit comprising
   an integral separation chamber, the separation chamber including:
     an inlet for introducing the multi-component composition;
     an inlet section communicating with the inlet; and
   a base section, arranged fixedly with respect to the inlet section and continuously communicating with the inlet section via a necked duct,
   wherein the necked duct is formed integrally with the inlet section and the base section as a narrowing in the separation chamber so as to spatially separate the inlet section from the base section and so as to allow detachment of said inlet section from said base section by physically separating them at the necked duct;
   and wherein the separation chamber is generally formed as a syringe and said is connectable with an extension nozzle or needle for drawing the multi-component composition;
   the kit further comprising a plunger, being slidably moveable within the base section of the separation chamber and operative to draw multi-component composition through said inlet into the separation chamber, the plunger including:
     a plunger base, slideable within said base section and
     a plunger handle, removably attached to the plunger base,
   wherein the plunger base includes a base through-hole extending therethrough and wherein the plunger handle is configured to seal the base through-hole when the plunger handle is attached to the plunger base and wherein the base through-hole is exposed when the plunger handle is removed from the plunger base;
   wherein the diameter of a lumen of the necked duct is selected so as to maintain any component of the multi-component composition within the inlet section by virtue of a partial negative pressure after covering said inlet and detaching said inlet section from said base section.

2. The kit according to claim 1, wherein the separation chamber further includes a housing surrounding the necked duct at the exterior of the separation chamber.

3. The kit according to claim 1, wherein the necked duct is configured to be detached by breaking or cutting.

4. The kit according to claim 1 further comprising a centrifugal tube, having a closed bottom and an opening and configured for introduction of the separation chamber into the centrifugal tube through the opening and facing the base through-hole with the bottom of the centrifugal tube.

5. The kit according to claim 4, wherein the centrifugal tube includes a cover for covering said opening and the inlet of the separation chamber, wherein the cover is configured so as to independently seal the inlet of the separation chamber and the opening of the centrifugal tube.

6. A method for centrifugal separation of a fraction of interest from a multi-component composition according to density by comprising:
   Providing an integral separation chamber, the separation chamber including:
     an inlet for introducing the multi-component composition
     an inlet section continuously communicating with the inlet; and
   a base section, arranged fixedly with respect to the inlet section and communicating with the
     the inlet section via a necked duct,
   wherein the necked duct is formed integrally with the inlet section and the base section as a narrowing in the separation chamber so as to spatially separate the inlet section from the base section and so as to allow detachment of said inlet section from said base section by physically separating them at the necked duct;
   and wherein the separation chamber is generally formed as a syringe and said inlet is connectable with an extension nozzle or a needle for drawing the multi-component composition;
   further providing a plunger being slidably moveable within the base section of the separation chamber and operative to draw multi-component composition through said inlet into the separation chamber, the plunger including:
     a plunger base, slideable within said base section and
     a plunger handle, removably attached to a plunger base,
   wherein the plunger base includes a base through-hole, extending therethrough, and wherein the plunger handle is configured to seal the base through-hole when the plunger handle is attached to the plunger base and wherein the base through-hole is exposed when the plunger handle is removed from the plunger base;
   and wherein the diameter of a lumen of the necked duct is selected so as to maintain any component of the multi-component composition within the inlet section by virtue of a partial negative pressure, after covering said inlet and detaching said inlet section from said base section
   the method further comprising the steps of:
     drawing the multi-component composition into the separation chamber through the inlet via the extension nozzle or the needle;

sealing the inlet by a cover and exposing the base through-hole by removing the plunger handle from the plunger base;

introducing a separator into the separation chamber via the exposed base through-hole;

performing centrifugation of the separation chamber; and detaching the inlet section from the base section of the separation chamber at the necked duct.

7. The method according to claim 6 wherein said drawing of the multi-component composition into the separation chamber is by means of said plunger and creates at least partial vacuum within the separation chamber.

8. The method according to claim 6 wherein the separation chamber further includes a housing surrounding the necked duct, the method further comprising removing the housing from the separation chamber after centrifugation and prior to detaching the separation chamber at the necked duct.

\* \* \* \* \*